US012662439B2

(12) United States Patent
Lee et al.

(10) Patent No.: US 12,662,439 B2
(45) Date of Patent: \*Jun. 23, 2026

(54) METHOD FOR PREPARATION OF 1, 4-CYCLOHEXANEDIMETHANOL

(71) Applicant: HANWHA SOLUTIONS CORPORATION, Seoul (KR)

(72) Inventors: Sun Uk Lee, Daejeon (KR); Namjin Jang, Daejeon (KR); Eun Jeong Kim, Daejeon (KR); Jong Kwon Lee, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 836 days.

This patent is subject to a terminal disclaimer.

(21) Appl. No.: 17/789,407

(22) PCT Filed: Dec. 28, 2020

(86) PCT No.: PCT/KR2020/019189

§ 371 (c)(1),
(2) Date: Jun. 27, 2022

(87) PCT Pub. No.: WO2021/133138

PCT Pub. Date: Jul. 1, 2021

(65) Prior Publication Data

US 2023/0054241 A1     Feb. 23, 2023

(30) Foreign Application Priority Data

Dec. 27, 2019    (KR) ........................ 10-2019-0176139
Dec. 24, 2020    (KR) ........................ 10-2020-0183548

(51) Int. Cl.

| | |
|---|---|
| *C07C 29/149* | (2006.01) |
| *B01J 21/18* | (2006.01) |
| *B01J 23/46* | (2006.01) |
| *B01J 23/62* | (2006.01) |
| *C07C 51/36* | (2006.01) |

(52) U.S. Cl.

CPC ............. *C07C 29/149* (2013.01); *B01J 21/18* (2013.01); *B01J 23/462* (2013.01); *B01J 23/626* (2013.01); *C07C 51/36* (2013.01); *C07C 2601/14* (2017.05)

(58) Field of Classification Search

CPC ............................... C07C 29/149; C07C 51/36
See application file for complete search history.

(56) References Cited

U.S. PATENT DOCUMENTS

| | | | |
|---|---|---|---|
| 2,917,549 A | 12/1959 | Knowles et al. |
| 6,495,730 B1 | 12/2002 | Konishi et al. |
| 6,919,489 B1 | 7/2005 | McCusker-Orth |
| 11,214,532 B2 | 1/2022 | Lee et al. |
| 11,629,112 B2 | 4/2023 | Jang et al. |

| | | | |
|---|---|---|---|
| 2005/0014973 A1 | 1/2005 | Endou et al. |
| 2012/0226069 A1 | 9/2012 | Fung et al. |
| 2015/0183699 A1 | 7/2015 | Hembre et al. |
| 2017/0107164 A1 | 4/2017 | Choi et al. |
| 2018/0346398 A1 | 12/2018 | Liao et al. |
| 2019/0062251 A1 | 2/2019 | Samant et al. |
| 2021/0061742 A1 | 3/2021 | Kim et al. |
| 2021/0070682 A1 | 3/2021 | Lee et al. |

FOREIGN PATENT DOCUMENTS

| | | |
|---|---|---|
| CN | 1926084 A | 3/2007 |
| CN | 102153469 A | 8/2011 |
| CN | 101982236 B | 7/2012 |
| CN | 109689606 A | 4/2019 |
| CN | 109776271 A | 5/2019 |
| JP | S36-000522 A | 9/1957 |
| JP | H02-131442 A | 5/1990 |
| JP | H2-131443 A | 5/1990 |
| JP | H07-047262 A | 2/1995 |
| JP | 2000-007595 A | 1/2000 |
| JP | 2000-080053 A | 3/2000 |
| JP | 2000-355564 A | 12/2000 |
| JP | 2001-145824 A | 5/2001 |
| JP | 2001-151716 A | 6/2001 |
| JP | 2002-020346 A | 1/2002 |
| JP | 2002-069016 A | 3/2002 |
| JP | 2002-069032 A | 3/2002 |
| JP | 2002-145824 A | 5/2002 |
| JP | 3629952 B2 | 3/2005 |
| JP | 2014-177422 A | 9/2014 |
| JP | 2014-524408 A | 9/2014 |
| JP | 6051980 B2 | 12/2016 |
| JP | 2017-515656 A | 6/2017 |
| KR | 2004-0047974 A | 6/2004 |

(Continued)

OTHER PUBLICATIONS

Machine translation of Patent No. KR20180035585A, Apr. 6, 2018; pp. 1-17 (Year: 2018).*
Machine translation of Patent No. KR101577362, Dec. 14, 2015 (Year: 2015).*
Machine translation WO2015129740A1, Sep. 3, 2015, pp. 1-19 (Year: 2015).*
Machine translation of WO2015178459A1, Nov. 26, 2015, pp. 1-73 (Year: 2015).*
International Search Report PCT/ISA/210 and Written Opinion PCT/ISA/237 for International Application No. PCT/KR2020/019189 Dated Apr. 7, 2021.

(Continued)

*Primary Examiner* — Medhanit W Bahta

(74) *Attorney, Agent, or Firm* — HARNESS, DICKEY & PIERCE, P.L.C.

(57) ABSTRACT

This invention relates to a method for preparing 1,4-cyclohexanedimethanol (CHDM), more specifically to a method for preparing 1,4-cyclohexanedimethanol having a high rate of trans isomers without an isomerization reaction step, wherein two-step hydrogenation reactions and a purification step are conducted using terephthalic acid as starting material.

15 Claims, No Drawings

(56) References Cited

FOREIGN PATENT DOCUMENTS

| KR | 10-0460371 | B1 | 12/2004 | | |
| KR | 100943872 | B1 | 2/2010 | | |
| KR | 101156312 | B1 | 6/2012 | | |
| KR | 10-2014-0058584 | A | 5/2014 | | |
| KR | 2015-0002258 | A | 1/2015 | | |
| KR | 2015-0062911 | A | 6/2015 | | |
| KR | 101577362 | B1 | 12/2015 | | |
| KR | 101619399 | B1 | 5/2016 | | |
| KR | 101639487 | B1 | 7/2016 | | |
| KR | 2018-0035585 | A | 4/2018 | | |
| KR | 10-2018-0047255 | A | 5/2018 | | |
| KR | 10-2019-0038062 | A | 4/2019 | | |
| KR | 10-2019-0076389 | A | 7/2019 | | |
| KR | 2019-0076389 | A | 7/2019 | | |
| KR | 2019-0081064 | A | 7/2019 | | |
| KR | 10-2020-0044109 | A | 4/2020 | | |
| KR | 2020/0081096 | A | 7/2020 | | |
| WO | WO-2015-102892 | A1 | 7/2015 | | |
| WO | WO-2015129740 | A1 * | 9/2015 | ............ | C07C 51/36 |
| WO | WO-2015178459 | A1 * | 11/2015 | .......... | C07C 29/149 |
| WO | WO-2019-046412 | A1 | 3/2019 | | |

OTHER PUBLICATIONS

Ansari et al., "Energy efficiency and performance of bubble generating systems", Dec. 29, 2017, Chemical Engineering & Processing: Process Intensification, vol. 125, pp. 44-55 (Year: 2017).

Xuefeng Li et al., One-Pot Conversion of Dimethyl Terephthalate into 1,4-Cyclohexanedimethanol with Supported Trimetallic RuPtSn Catalysts, Industrial & Engineering Chemistry Research 2014 53 (2), 619-625; DOI: 10.1021/ie402987c.

María José Nieves-Remacha et al., Gas-Liquid Flow and Mass Transfer in an Advanced-Flow Reactor, Industrial & Engineering Chemistry Research 2013 52 (26), 8996-9010; DOI: 10.1021/ie4011707.

* cited by examiner

1

METHOD FOR PREPARATION OF 1, 4-CYCLOHEXANEDIMETHANOL

BACKGROUND OF THE INVENTION

(a) Field of the Invention

CROSS-REFERENCE TO RELATED APPLICATIONS

This application is a national phase under 35 U.S.C. § 371 of PCT International Application No. PCT/KR2020/019189 which has an International filing date of Dec. 28, 2020, which claims priority to Koream Patent Application Nos. 10-2019-0176139, filed Dec. 27, 2019 and 10-2020-0183548, filed Dec. 24, 2020 the entire contents of each of which are hereby incorporated by reference.

This invention relates to method for preparing 1,4-cyclohexanedimethanol (CHDM). More specifically, this invention relates to a method for preparing 1,4-cyclohexanedimethanol having a high rate of trans isomers without an isomerization reaction step, wherein two-step hydrogenation reactions and a purification step are conducted using terephthalic acid as starting material.

(b) Description of the Related Art 1,4-cyclohexanedimethanol(CHDM) is widely used as the raw material of medicine, synthetic resin, synthetic fiber or dye, and the like, and particularly, used as the raw material of environment-friendly polyethyleneterephthalate.

1,4-cyclohexanedimethanol exists as stereoisomers of cis and trans forms, and for higher quality product, it is required to have a higher rate of trans 1,4-cyclohexanedimethanol (trans CHDM) than cis CHDM.

Among the methods for preparing 1,4-cyclohexanedimethanol, a method by the hydrogenation reaction of dimethyl terephthalate(DMT) is commercially mainly used. According to this method, phthalate is reacted with methanol to prepare DMT, followed by two-step hydrogenation to prepare 1,4-cyclohexanedimethanol. The first hydrogenation reaction converts DMT into DMCD(diester dimethyl 1,4-cyclohexanedicarboxylate), and the second hydrogenation reaction converts DMCD into CHDM. Wherein, the ratio of cis CHDM and trans CHDM is determined according to the kind of a catalyst. In case a copper chromite catalyst, which is commercially mainly used copper chrome oxide, is used, the ratio of cis CHDMA and trans CHDM may become about 3:7. Since this method uses DMT and involves a trans esterification reaction using methanol, reaction and separation processes are complicated, and for isomerization, additives should be added so as to influence the quality of the final product.

According to another method, phthalate is first hydrogenated and converted into 1,4-cyclohexane dicarboxylic acid (CHDA), and CHDA is hydrogenated into CHDM. This method uses a heterogeneous catalyst and consists of two step hydrogenation reactions.

Korean Laid-Open Patent Publication No. 2015-0062911 suggested a method for preparing CHDM through two step reduction processes, wherein terephthalic acid is reduced in the presence of a first metal catalyst comprising a palladium (Pd) compound, and the reduction product of the terephthalic acid is reduced in the presence of a second metal catalyst comprising a ruthenium(Ru) compound, a tin(Sn) compound and a platinum(Pt) compound at the weight ratio of 1:0.8 to 1.2: 0.2 to 0.6, in one reactor, without an isomerization reaction. However, this method does not pass through an isomerization reaction, and thus, has a problem of low trans CHDM rate.

Korean Registered Patent No. 0943872 suggested a method of separating intermediate trans CHDA so as to increase trans CHDM rate. According to this method, simultaneously with progressing an isomerization reaction using melting point difference between cis CHDA and trans CHDA, trans CHDA is produced as a solid or molten state. However, this method requires a process of removing water used as a solvent or other solvents, and should be operated at low temperature to remove heat used in the reduction process of phthalate for recrystallization, and thus, is not economically efficient.

As another method, Japanese Laid-Open Patent Publication No. 2014-177422 suggested a method of obtaining desired trans CHDM rate by controlling the temperature and time of hydrogenation reaction. This method progresses an isomerization reaction simultaneously with a reduction reaction of CHDA, and adopts means for controlling reaction temperature and reaction time in a fixed bed reactor, but the fixed bed reactor easily progresses crystallization during conversion of reactant CHDA, and catalyst performance decreases by crystallization, and thus, desired yield and trans CHDM rate cannot be achieved.

PATENT DOCUMENT (Patent Document 0001) Korean Laid-Open Patent Publication No. 2015-0062911 호

(Patent Document 0002) Korean Registered Patent No. 0943872

(Patent Document 0003) Japanese Laid-Open Patent Publication No. 2014-177422

SUMMARY OF THE INVENTION

In order to solve the problems of the prior art, it is an object of the invention to provide a method for stably preparing 1,4-cyclohexanedimethanol having a high rate of trans isomers with high yield without an isomerization reaction step, by conducting two-step hydrogenation reactions using terephthalic acid as starting material, and controlling the content of raw material terephthalic acid and the content of 1,4-cyclohexane dicarboxylic acid(CHDA).

According to one aspect of the invention, there is provided a method for preparing 1,4-cyclohexanedimethanol comprising:

a step 1 wherein a reaction solution comprising terephthalic acid, a first hydrogenation catalyst, and water is supplied to a first reactor equipped with a stirrer, and a hydrogenation reaction is conducted to prepare 1,4-cyclohexane dicarboxylic acid(CHDA) comprising cis isomers and trans isomers; and a step 2 wherein a reaction solution comprising a reaction product of the step 1, a second hydrogenation catalyst, and water is supplied to a second reactor equipped with a stirrer, and a hydrogenation reaction is conducted to prepare 1, 4-cyclohexanedimethanol(CHDM) comprising cis isomers and trans isomers.

According to another aspect of the invention, there is provided a composition comprising 1,4-cyclohexanedimethanol prepared by the method.

According to the preparation method of 1,4-cyclohexanedimethanol of the invention, 1,4-cyclohexanedimethanol can be prepared with high yield by continuous hydrogenation reactions using terephthalic acid as starting material, and without conducting an isomerization reaction step, 1,4-cyclohexanedimethanol having a high rate of trans isomers in the cis isomers and trans isomers of 1,4-cyclohexanedimethanol can be stably prepared.

And, according to the preparation method of the invention, the step 2 hydrogenation process is conducted using the step 1 hydrogenation reaction product of terephthalic acid without additional purification or separation process, thus simplifying the process, and hydrogenation may be conducted while maintaining the reaction temperature of the hydrogenation reaction step of terephthalic acid, and thus, thermal energy loss may not be generated, which is economical.

According to the preparation method, additional isomerization step is not conducted, and thus, the process is simplified and economical, and the content of trans isomers in the prepared 1,4-cyclohexanedimethanol is high, and thus, property improvement may be expected when using it as the raw material of polymer.

DETAILED DESCRIPTION OF THE EMBODIMENTS

The terms used herein are only to explain specific embodiments, and are not intended to limit the invention. A singular expression includes a plural expression thereof, unless it is expressly stated or obvious from the context that such is not intended. As used herein, the terms "comprise", "equipped" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Although various modifications can be made to the invention and the invention may have various forms, specific examples will be illustrated and explained in detail below. However, it should be understood that these are not intended to limit the invention to specific disclosure, and that the invention includes all the modifications, equivalents or replacements thereof without departing from the spirit and technical scope of the invention.

Hereinafter, a method for preparing 1,4-cyclohexanedimethanol according to specific embodiments of the invention will be explained in detail.

The method for preparing 1,4-cyclohexanedimethanol of the invention comprises: a step 1 wherein a reaction solution comprising terephthalic acid, a first hydrogenation catalyst, and water is supplied to a first reactor equipped with a stirrer, and a hydrogenation reaction is conducted to prepare 1,4-cyclohexane dicarboxylic acid(CHDA) comprising cis isomers and trans isomers; and a step 2 wherein a reaction solution comprising a reaction product of the step 1, a second hydrogenation catalyst, and water is supplied to a second reactor equipped with a stirrer, and a hydrogenation reaction is conducted to prepare 1, 4-cyclohexanedimethanol(CHDM) comprising cis isomers and trans isomers.

Previously, in order to prepare 1,4-cyclohexanedimethanol having a high content of trans isomers, an isomerization reaction step for converting cis isomers into trans isomers was necessarily involved. For example, using 1,4-cyclohexane dicarboxylic acid as the raw material of an isomerization reaction, 1,4-cyclohexane dicarboxylic acid having increased trans content was obtained, and then, it was used again as the raw material of a hydrogenation reaction to prepare 1,4-cyclohexanedimethanol having high trans content, or raw material 1,4-cyclohexane dicarboxylic acid was first hydrogenated, and then, obtained 1,4-cyclohexanedimethanol was subjected to an isomerization reaction to prepare 1,4-cyclohexanedimethanol having increased trans content. However, in case 1,4-cyclohexanedimethanol is prepared by the previous method, due to the additional isomerization process, the process is complicated and inefficient, and additional production cost is required, which is not commercially preferable.

Thus, the method for preparing 1,4-cyclohexanedimethanol according to one embodiment of the invention is based on the discovery that by conducting a hydrogenation reaction using terephthalic acid as starting material, 1,4-cyclohexane dicarboxylic acid comprising a high content of trans isomers can be prepared without an isomerization reaction step for converting cis isomers into trans isomers. And, by conducting a hydrogenation reaction using the 1,4-cyclohexane dicarboxylic acid thus prepared, 1,4-cyclohexanedimethanol comprising a high content of trans isomers can be also prepared.

In case a hydrogenation reaction of terephthalic acid is conducted in the presence of a hydrogenation catalyst to prepare 1,4-cyclohexane dicarboxylic acid, 1,4-cyclohexane dicarboxylic acid obtained as the reaction product is in the form of a mixture of cis isomers and trans isomers, namely, cis CHDA and trans CHDA.

According to Korean Laid-Open Patent Publication No. 2020-0081096, it is disclosed that as the result of the hydrogenation reaction of terephthalic acid, a mole ratio of cis isomers and trans isomers is about 8:2 to about 6:4, thus obtaining more cis isomers, and that the mole ratio of cis isomers and trans isomers is generally within the above range regardless of the kind of the hydrogenation catalyst or detailed conditions of the hydrogenation reaction.

Thus, previously, in order to prepare 1,4-cyclohexane dicarboxylic acid having high trans content, a hydrogenation reaction of terephthalic acid into 1,4-cyclohexane dicarboxylic acid was conducted, and then, an isomerization reaction step for converting cis isomers of 1,4-cyclohexane dicarboxylic acid into trans isomers of 1,4-cyclohexane dicarboxylic acid was necessarily conducted. However, such a method is complicated and inefficient and requires additional production cost, due to the isomerization process, and thus, is not commercially preferable.

Meanwhile, the preparation method according to one embodiment of the invention conducts two-step continuous hydrogenation reactions in a multi-staged reactor using terephthalic acid as starting material, and can finally prepare 1,4-cyclohexanedimethanol having a high content of trans isomers without an isomerization reaction step for converting cis isomers into trans isomers.

And, by controlling the concentration of raw material terephthalic acid, 1,4-cyclohexane dicarboxylic acid comprising a high content of trans isomers can be prepared only by a hydrogenation process.

When progressing a hydrogenation reaction of a compound having cis/trans isomers, it is generally expected that cis and trans ratios of the reactant and product before and after the reaction may be maintained without significant change. Even if the concentration of the reactant is increased, only improvement in the reaction speed may be anticipated, and commonly, change in isomer ratio of the hydrogenation reaction product is not expected.

However, according to one embodiment of the invention, when the concentration of terephthalic acid is within a specific range, trans isomer content of the product 1,4-cyclohexane dicarboxylic acid unexpectedly increases without additional isomerization reaction step.

5

And, in the next step of the hydrogenation reaction of 1,4-cyclohexane dicarboxylic acid, when the concentration of 1,4-cyclohexane dicarboxylic acid is within a specific range, trans isomer content of the product 1,4-cyclo-hexanedimethanol unexpectedly increases without additional isomerization reaction step. It is believed that the isomerization speed varies according to the concentration of hydrogenation reaction subject and the concentration of a hydrogenation catalyst, and at specific concentrations, the isomerization speed increases and a time for reaching the equilibrium of trans/cis isomer ratio is shortened.

Thus, the method for preparing 1,4-cyclohexanedimetha-nol of the invention is a method capable of stably preparing 1,4-cyclohexanedimethanol having a high rate of trans iso-mers without conducting an isomerization step, wherein two step hydrogenation reactions are conducted in a multi-staged reactor using terephthalic acid as starting material.

Thus, according to the preparation method of 1,4-cyclo-hexanedimethanol of the invention, 1,4-cyclohexanedime-thanol can be prepared with high yield, and 1,4-cyclo-hexanedimethanol having a high rate of trans isomers in cis isomers and trans isomers of 1,4-cyclohexanedimethanol can be prepared.

Hereinafter, a method for preparing 1,4-cyclohexanedi-methanol according to one embodiment of the invention will be explained according to steps.

Step 1

In the step 1, a reaction solution comprising terephthalic acid, a first hydrogenation catalyst, and water is supplied to a first reactor equipped with a stirrer, and a hydrogenation reaction is conducted to prepare 1,4-cyclohexane dicarbox-ylic acid comprising cis isomers and trans isomers.

By the hydrogenation reaction of step 1, the aromatic ring of terephthalic acid is hydrogenated and converted into 1,4-cyclohexane dicarboxylic acid corresponding thereto.

More specifically, in a first reactor equipped with a stirrer, a reaction solution comprising terephthalic acid, a first hydrogenation catalyst, and water is introduced.

The terephthalic acid is included in the content of 5 to 25 wt %, based on the total amount of terephthalic acid and water. More specifically, the content of the terephthalic acid may be 5 wt % or more, or 10 wt % or more, or 15 wt % or more, or 18 wt % or more, and 25 wt % or less, or 24 wt % or less, or 22 wt % or less, based on the total amount of terephthalic acid and water.

If the content of the terephthalic acid is less than 5 wt % based on the total amount of terephthalic acid and water, it takes a long time to reach the equilibrium of trans/cis isomer ratio, and thus, the rate of trans isomers in produced CHDA may be low, and if it is greater than 25 wt %, due to low solubility of terephthalic acid, it is difficult to dissolve, and a reaction temperature should be set high. If the reaction temperature increases, low boiling by-products may be generated in large quantities, thus decreasing yield, and catalytic activity may decrease due to thermal fatigue.

According to one embodiment of the invention, as the first hydrogenation catalyst, catalysts known to be usable for a hydrogenation reaction of terephthalic acid may be used.

According to one embodiment of the invention, the first hydrogenation catalyst may comprise one or more metals selected from the group consisting of palladium(Pd), rhodi-um(Rh), ruthenium(Ru), and platinum(Pt), as an active component.

Preferably, the first hydrogenation catalyst may comprise palladium(Pd) as an active component.

According to one embodiment of the invention, the amount of the active component of the first hydrogenation catalyst may be appropriately controlled according to the content of terephthalic acid. Specifically, as the content of the catalyst is higher compared to terephthalic acid, a reaction speed increases, and thus, the hydrogenation cata-lyst may be added in such an amount that the weight ratio of the first hydrogenation catalyst and terephthalic acid may become 0.01:1 or more.

However, in case the content of the first hydrogenation catalyst is above a certain level compared to terephthalic acid, the reaction speed increasing effect may be insignifi-cant compared to the amount used, and thus, reaction efficiency may decrease. Thus, the first hydrogenation cata-lyst may be more specifically added in an amount fulfilling the weight ratio of the first hydrogenation catalyst and terephthalic acid of 0.01:1 to 3:1, or 0.01:1 to 2.5:1, or 0.1:1 to 2:1.

However, the scope of the invention is not limited by the above weight ratio, and the rate of the catalyst may be appropriately controlled according to specific reaction con-ditions and the kind of a reactor.

The first hydrogenation catalyst may be supported on a carrier, and as the carrier, those known in the art may be used without limitations. Specifically, carbon, zirconia($ZrO_2$), titania ($TiO_2$), alumina($Al_2O_3$), or silica($SiO_2$), and the like may be used.

When carbon is used as the carrier, although not limited, at least one selected from the group consisting of activated carbon, carbon black, graphite, graphene, OMC (ordered mesoporous carbon) and carbon nanotube may be used.

Preferably, it may be carbon black having a high rate of mesopores in the total pores, and specifically, the activated carbon may be SXULTRA, CGSP, PK1-3, SX 1G, DRACO S51HF, CA-1, A-51, GAS 1240 PLUS, KBG, CASP and SX PLUS, and the like, and the carbon black may be BLACK PEARLS®, ELFTEX®, VULCAN®, MOGUL®, MON-ARCH®, EMPEROR®, and REGAL®, and the like, but not limited thereto.

Wherein, according to the invention, in the carbon carrier, the volume fraction of mesopores having sizes of 2 to 50 nm in the total pores may be 50% or more. Preferably, in the carbon carrier, the volume fraction of mesopores in the total pores may be 70% or more, and more preferably, in the carbon carrier, the volume fraction of mesopores in the total pores may be 75% or more.

Wherein, if the volume fraction of mesopores is less than 50%, there may be a problem in terms of a speed of microscopic transfer of the reactant and product in the carbon carrier, and if the average size of the pores is greater than 50 nm, the physical strength of the carrier may be weak, and thus, the above ranges are preferable.

And, according to the invention, the carbon comprises ordered mesoporous carbon(OMC) having specific surface area(BET) of 100 to 1,500 $m^2$/g. Preferably, the carbon may comprise ordered mesoporous carbon(OMC) having specific surface area(BET) of 200 to 1,000 $m^2$/g. Wherein, if the specific surface area of carbon is less than 100 $m^2$/g, it may be difficult to highly disperse active metal, and if the specific surface area of carbon is greater than 1,500 $m^2$/g, the rate of mesopores may decrease, and thus, the above ranges are preferable.

And, in some cases, the carbon carrier of the catalyst according to the invention comprises an appropriate rate of micropores, besides mesopores, and preferably, the volume fraction of micropores may be 0 to 25% in the total pores. Wherein, in case the volume fraction of micropores is greater than 25%, there may be a problem in terms of a speed of microscopic transfer of reactant and product in the carbon carrier, and thus, the above range is preferable.

In case the first hydrogenation catalyst is supported on a carrier, the amount of the active component of the first hydrogenation catalyst may be preferably 20 parts by weight or less, based on 100 parts by weight of the carrier, and it may be 15 parts by weight or less, or 10 parts by weight or less, and 1 part by weight or more, or 3 parts by weight or more. If the amount of the first hydrogenation catalyst is too large based on 100 parts by weight of the carrier, a reaction may rapidly progress on the catalyst surface, during which side reactions may also increase and the amount of by-products may rapidly increase, and if the amount of the first hydrogenation catalyst is too small, catalyst amount may be insufficient, and thus, yield of the hydrogenation reaction may decrease, and thus, the above range is preferable.

The step 1 may be conducted using a first reactor comprising a stirrer, a raw material inlet, a metal sintered filter, and a product outlet.

For example, the stirrer may be a gas-induced type stirrer comprising a gas inlet, a gas passage, an impeller and jet orifices.

More specifically, the stirrer is provided in the up and down direction of the first reactor, and the upper part may be provided with a gas inlet for inhaling gas, namely, hydrogen gas by centrifugal force. The hydrogen gas inhaled in the gas inlet is passed to the lower part of the reactor through the gas passage. The hydrogen gas passed to the lower part of the reactor is sprayed and fed into the reaction solution through plural jet orifices of the stirrer, thus conducting a hydrogenation reaction. The jet orifice may be positioned at the lower part, on the side, or both at the lower part and on the side of the stirrer.

As such, as a hydrogenation reaction is conducted while spraying and mixing hydrogen gas inhaled through the gas inlet into the reaction solution through the plural jet orifices of the stirrer, hydrogenation reaction speed may increase.

And, since the stirrer comprises an impeller stirring the reaction solution, gas holdup and surface area per unit volume may increase. Thus, a hydrogenation reaction speed in the reactor may increase.

The impeller may be arranged in multi stages at the rotation axis of the stirrer.

Alternatively, according to another embodiment, only an impeller having jet orifices may be provided at the lower part of the stirrer, and additional impellers may not be provided.

The rotation axis may be operated by a driving motor equipped outside.

The lower part of the first reactor may be connected to the raw material inlet, and raw materials, namely, terephthalic acid, solvents, and hydrogen gas may be introduced therein.

Meanwhile, the first reactor may comprise a metal sintered filter for filtering a catalyst from the product, and a product outlet, wherein the metal sintered filter may be connected to the product outlet and installed. And, the metal sintered filter may be connected to the product outlet and provided outside of the reactor. The metal sintered filter may effectively filter catalyst components remaining in the product.

Next, in the first reactor where the reaction solution is introduced, hydrogen gas is fed.

The hydrogenation reaction may be conducted in liquid phase or gas phase. According to one embodiment of the invention, a hydrogenation reaction may be progressed while terephthalic acid is a liquid phase dissolved in a solvent such as water, and hydrogen is a gas phase, Next, by stirring the stirrer of the first reactor to conduct a hydrogenation reaction, 1,4-cyclohexane dicarboxylic acid is prepared.

Although the hydrogenation reaction conditions are not specifically limited herein, for example, a reaction temperature may be 230° C. or more, and 300° C. or less, or 280° C. or less, or 270° C. or less. If the reaction temperature is less than 230° C., contact with a catalyst may decrease or the temperature may not fall within a temperature at which the catalyst is activated, and thus, a reaction speed may decrease, or the content of trans isomers in produced CHDA may decrease, and if the reaction temperature is greater than 300° C., by-products may rapidly increase, and catalyst life may be also influenced, and thus, the above range is preferable.

And, a reaction pressure may be 50 bar or more, or 80 bar or more, and 220 bar or less, or 200 bar or less, or 180 bar or less. If the reaction pressure is less than 50 bar, a reaction may not sufficiently occur, and thus, an excessive amount of catalyst may be consumed, and residence time may be too lengthened, thus causing a lot of problems such as by-product increase, and if the reaction pressure is greater than 220 bar, excessive energy may be required during process operation, and the production cost of equipment such as a reactor may significantly increase, and thus, the above range is preferable.

Since the reaction pressure is a pressure established by hydrogen gas supplied, it may be controlled according to the amount of hydrogen gas supplied.

During the hydrogenation reaction, a stirring process is conducted, and the reaction efficiency of the hydrogenation reaction may be increased through control of the stirring speed. Specifically, the stirring process may be conducted such that the surface area per unit volume of hydrogen gas bubbles may become 15 $m^2/m^3$ or more, more specifically, 50 $m^2/m^3$ or more, or 100 $m^2/m^3$ or more, or 150 $m^2/m^3$ or more, or 200 $m^2/m^3$ or more, or 300 $m^2/m^3$ or more.

As long as the surface area per unit volume meets a certain level, for example, 15 $m^2/m^3$ or more, a reaction speed is slower than a speed at which hydrogen gas is dissolved, and thus, a reaction speed may not be significantly influenced. Thus, the upper limit of the surface area per unit volume is not specifically limited as long as it meets 15 $m^2/m^3$ or more, but considering the energy efficiency of a reactor, it is preferably 500 $m^2/m^3$ or less.

Meanwhile, the stirring process may be conducted using the stirrer of the first reactor as explained above.

It may be more preferable in terms of process efficiency that the reaction is conducted for 1 to 10 hours under conditions fulfilling all the hydrogenation reaction conditions as described above.

In the reaction product obtained after the step 1, CHDA comprising cis isomers and trans isomers, solvent water, and a catalyst, and the like are included, and it is used as the reactant of the subsequent hydrogenation reaction of step 2 (hydrogenation reaction of CHDA to CHDM). It may be sent as the reactant of the hydrogenation reaction of step 2, after removing the catalyst included in the reaction product by a catalyst filter, and the like, as necessary.

According to one embodiment of the invention, in the reaction product of step 1, the amount of 1,4-cyclohexane dicarboxylic acid comprising cis isomers and trans isomers may be 5 to 30 wt %, based on the total amount of 1,4-cyclohexane dicarboxylic acid and water. More specifically, it may be 5 wt % or more, or 7 wt % or more, or 10 wt % or more, and 30 wt % or less, or 25 wt % or less, or 23 wt % or less.

According to one embodiment of the invention, in the mixed solution comprising terephthalic acid, a first hydrogenation catalyst and water, the amount of terephthalic acid may be 5 to 25 wt %, preferably 10 to 25 wt %, more preferably, 12 to 22 wt %, based on the total amount of terephthalic acid and water. In case the mixed solution comprising the above content of terephthalic acid is subjected to a hydrogenation reaction to prepare 1,4-cyclohexane dicarboxylic acid, in the total 1,4-cyclohexane dicarboxylic acid prepared, the rate of trans isomers may be 60 wt % or more, or 62 wt % or more, or 65 wt % or more, or 67 wt % or more, or 70 wt % or more, and although there is no upper limit of the trans isomer rate, for example, it may be 80 wt % or less, or 78 wt % or less, or 75 wt % or less.

As explained above, 1,4-cyclohexane dicarboxylic acid obtained by the hydrogenation reaction of step 1 has high trans isomer content of 60 wt % or more, and thus, can be usefully used as the reactant of the hydrogenation reaction of step 2, without additional isomerization process.

Step 2

In the step 2, a reaction solution comprising a reaction product of step 1, a second hydrogenation catalyst, and water is introduced in a second reactor equipped with a stirrer, and a hydrogenation reaction is conducted, thus preparing 1, 4-cyclohexanedimethanol(CHDM) comprising cis isomers and trans isomers.

More specifically, in a second reactor equipped with a stirrer, a reaction solution comprising a reaction product of step 1, a second hydrogenation catalyst, and water is introduced.

In the reaction product of step 1, 1,4-cyclohexane dicarboxylic acid, a first hydrogenation catalyst, and solvent water are included, and it may be used as the reactants of the hydrogenation reaction of step 2. Wherein, it is preferable that the first hydrogenation catalyst included in the reaction product of step 1 is removed by a filter, and the like, before conducting step 2.

And, besides 1,4-cyclohexane dicarboxylic acid, solvent water is included in the reaction product of step 1, and thus, it may be used in step 2 reaction without introducing additional water. Alternatively, if necessary, in order to control the concentration of the reaction solution, water may be partly removed or additionally introduced.

The 1,4-cyclohexane dicarboxylic acid is included in the amount of 5 to 30 wt %, based on the total amount of 1,4-cyclohexane dicarboxylic acid and water. More specifically, it may be included in the amount of 5 wt % or more, or 7 wt % or more, or 10 wt % or more, and 30 wt % or less, or 25 wt % or less, or 23 wt % or less, based on the total amount of 1,4-cyclohexane dicarboxylic acid and water.

If the amount of 1,4-cyclohexane dicarboxylic acid is less than 5 wt %, based on the total amount of 1,4-cyclohexane dicarboxylic acid and water, contact between reactants and catalyst may decrease, and thus, a reaction speed may decrease, or the rate of trans isomers may decrease in produced CHDM, and if it is greater than 30 wt %, solubility of 1,4-cyclohexane dicarboxylic acid may be lowered, and thus, productivity may decrease, and precipitates of the reactants and catalyst amount may increase, thus causing a difficulty in feeding of slurry.

Wherein, the rate of cis isomers and trans isomers of the raw material 1,4-cyclohexane dicarboxylic acid is identical to the rate of cis isomers and trans isomers of 1,4-cyclohexane dicarboxylic acid obtained in the hydrogenation reaction of step 1. Thus, the 1,4-cyclohexane dicarboxylic acid may have trans isomer rate of 60 wt % or more, or 62 wt % or more, or 65 wt % or more, or 67 wt % or more, or 70 wt % or more, and although there is no upper limit of trans isomer rate, for example, it may be 80 wt % or less, or 78 wt % or less, or 75 wt % or less.

According to one embodiment of the invention, the second hydrogenation catalyst may comprise one or more metals selected from the group consisting of palladium(Pd), rhodium(Rh), and ruthenium(Ru), and one or more metals selected from the group consisting of tin(Sn), iron(Fe), rhenium(Re), and gallium(Ga), as active components.

Preferably, the second hydrogenation catalyst may comprise ruthenium(Ru) and tin(Sn) as active components. More preferably, the active components of the hydrogenation catalyst may consist only of ruthenium(Ru) and tin(Sn), and other active components may not be included.

According to one embodiment of the invention, the amount of the active components of the second hydrogenation catalyst may be appropriately controlled according to the content of reactant CHDA. Specifically, as the content of the second hydrogenation catalyst based on CHDA is higher, a reaction speed increases, and thus, the second hydrogenation catalyst may be added in such an amount that the weight ratio of the second hydrogenation catalyst and CHDA may become 0.01:1 or more.

However, if the content of the second hydrogenation catalyst based on CHDA is above a certain level, the reaction speed increase effect may be insignificant compared to the amount used, thus decreasing reaction efficiency, and thus, the second hydrogenation catalyst may be more specifically added in such an amount that the weight ratio of the second hydrogenation catalyst and CHDA may fulfill 0.01:1 to 3:1.

Considering the reaction speed improvement effect according to control of the weight ratio of the second hydrogenation catalyst and CHDA, it may be more preferable to add the second hydrogenation catalyst in such an amount that the weight ratio of the second hydrogenation catalyst and CHDA may become 0.01:1 to 3:1, or 0.1:1 to 3:1, or 0.1:1 to 2:1.

However, the scope of the invention is not limited by the above weight ratio, and the rate of a catalyst may be appropriately controlled according to detailed reaction conditions, and the kind of a reactor.

Such a second hydrogenation catalyst may be supported on a carrier, and as the carrier, those known in the art may be used without limitations. Specifically, carbon, zirconia ($ZrO_2$), titania($TiO_2$), alumina($Al_2O_3$), or so;oca($SiO_2$), and the like may be used.

According to one embodiment of the invention, in case the second hydrogenation catalyst comprises ruthenium(Ru) and tin(Sn) as active components, ruthenium(Ru) and tin (Sn) may be included respectively in an amount of 1 to 20 parts by weight, or 1 to 10 parts by weight, or 3 to 8 parts by weight, based on 100 parts by weight of the carrier.

When carbon is used as the carrier, although not limited, at least one selected from the group consisting of activated carbon, carbon black, graphite, graphene, OMC (ordered mesoporous carbon) and carbon nanotube may be used.

Preferably, it may be carbon black having a high rate of mesopores in the total pores, and specifically, the activated carbon may be SXULTRA, CGSP, PK1-3, SX 1G, DRACO S51HF, CA-1, A-51, GAS 1240 PLUS, KBG, CASP and SX PLUS, and the like, and the carbon black may be BLACK PEARLS®, ELFTEX®, VULCAN®, MOGUL®, MONARCH®, EMPEROR®, and REGAL®, and the like, but not limited thereto.

Wherein, according to the invention, in the carbon carrier, the volume fraction of mesopores having sizes of 2 to 50 nm in the total pores may be 50% or more. Preferably, in the carbon carrier, the volume fraction of mesopores in the total pores may be 70% or more, and more preferably, in the carbon carrier, the volume fraction of mesopores in the total pores may be 75% or more.

Wherein, if the volume fraction of mesopores is less than 50%, there may be a problem in terms of a speed of microscopic transfer of reactant and product in the carbon carrier, and if the average size of the pores is greater than 50 nm, the physical strength of the carrier may be weak, and thus, the above ranges are preferable.

And, according to the invention, the carbon comprises ordered mesoporous carbon(OMC) having specific surface area(BET) of 100 to 1,500 m$^2$/g. Preferably, the carbon may comprise ordered mesoporous carbon(OMC) having specific surface area(BET) of 200 to 1,000 m$^2$/g. Wherein, if the specific surface area of carbon is less than 100 m$^2$/g, it may be difficult to highly disperse active metals(Ru, Sn), and if the specific surface area of carbon is greater than 1,500 m$^2$/g, the fraction of mesopores may decrease, and thus, the above ranges are preferable.

And, in some cases, the carbon carrier of the catalyst according to the invention comprises an appropriate fraction of micropores, besides mesopores, and preferably, the volume fraction of micropores may be 0 to 25% in the total pores. Wherein, in case the volume fraction of micropores is greater than 25%, there may be a problem in terms of a speed of microscopic transfer of reactant and product in the carbon carrier, and thus, the above range is preferable.

The step 2 may be conducted using a second reactor comprising a stirrer, a raw material inlet, a metal sintered filter, and a product outlet.

The second reactor is as explained about the first reactor in step 1, and thus, the explanations are omitted.

Next, in the reactor where the reaction solution is introduced, hydrogen gas is fed.

The hydrogenation reaction may be conducted in liquid phase or gas phase. According to one embodiment of the invention, a hydrogenation reaction may be progressed while 1,4-cyclohexane dicarboxylic acid is a liquid phase dissolved in a solvent such as water, and hydrogen is a gas phase, Next, by stirring the stirrer of the second reactor to conduct a hydrogenation reaction, 1,4-cyclohexanedimethanol is prepared.

Although the hydrogenation reaction conditions are not specifically limited in this invention, for example, a reaction temperature may be 230° C. or more, and 300° C. or less, or 280° C. or less, or 270° C. or less. If the reaction temperature is less than 230° C., contact between reactants and catalyst may decrease or the temperature may not fall within a temperature at which the catalyst is activated, and thus, a reaction speed may decrease, or the content of trans isomers in produced CHDM may decrease, and if the reaction temperature is greater than 300° C., by-products may rapidly increase, and catalyst life may be also influenced, and thus, the above range is preferable.

And, a reaction pressure may be 50 bar or more, or 80 bar or more, and 220 bar or less, or 200 bar or less, or 180 bar or less. If the reaction pressure is less than 50 bar, a reaction may not sufficiently occur, and thus, an excessive amount of catalyst may be consumed, and residence time may be too lengthened, thus causing a lot of problems such as by-product increase, and if the reaction pressure is greater than 220 bar, excessive energy may be required during process operation, and the production cost of equipment such as a reactor may significantly increase, and thus, the above range is preferable.

Since the reaction pressure is a pressure established by hydrogen gas supplied, it may be controlled according to the amount of hydrogen gas supplied.

During the hydrogenation reaction, a stirring process is conducted, and the reaction efficiency of the hydrogenation reaction may be increased through control of stirring speed. Specifically, the stirring process may be conducted such that the surface area per unit volume of hydrogen gas bubbles may become 15 m$^2$/m$^3$ or more, more specifically, 50 m$^2$/m$^3$ or more, or 100 m$^2$/m$^3$ or more, or 150 m$^2$/m$^3$ or more, or 200 m$^2$/m$^3$ or more, or 300 m$^2$/m$^3$ or more.

As long as the surface area per unit volume meets a certain level, for example, 15 m$^2$/m$^3$ or more, a reaction speed may be slower than a speed at which hydrogen gas is dissolved, and thus, a reaction speed may not be significantly influenced. Thus, the upper limit of the surface area per unit volume is not specifically limited as long as it meets 15 m$^2$/m$^3$ or more, but considering the energy efficiency of a reactor, it is preferably 500 m$^2$/m$^3$ or less.

Meanwhile, the stirring process may be conducted using the stirrer of the reactor as explained above.

It may be more preferable in terms of process efficiency that the reaction is conducted for 1 to 10 hours under conditions fulfilling all the hydrogenation reaction conditions as described above.

In the reaction product obtained after step 2, CHDM comprising cis isomers and trans isomers, solvent water, and a catalyst, and the like are included, and it may be used as the reactants of various reactions. It may be used, after removing by-products, solvents and catalysts, and the like included in the reaction product by a purification process, as necessary.

According to one embodiment of the invention, in the reaction product of step 2, the amount of CHDM comprising cis isomers and trans isomers may be 5 to 30 wt %, based on the total amount of the reaction product of the step. More specifically, it may be 5 wt % or more, or 7 wt % or more, or 10 wt % or more, and 30 wt % or less, or 25 wt % or less, or 23 wt % or less.

In order to immediately use 1,4-cyclohexanedimethanol as the raw material or reactant of other processes without an isomerization process, the content of trans isomers in 1,4-cyclohexanedimethanol should be 63 wt % or more.

According to one embodiment of the invention, the reaction product of step 2, i.e., 1,4-cyclohexanedimethanol may have a very high content of trans isomers, such as 63 wt % or more, or 65 wt % or more, or 67 wt % or more, or 69 wt % or more, or 70 wt % or more. And, although there is no upper limit of the rate of trans isomers, for example, it may be 99 wt % or less, or 95 wt % or less, or 90 wt % or less, or 85 wt % or less.

As explained above, 1,4-cyclohexanedimethanol obtained after the hydrogenation reaction of step 2 has high trans isomer content, and thus, can be usefully used as the raw material for preparing high quality products, without additional isomerization process.

Step 3

According to one embodiment of the invention, the method for preparing 1,4-cyclohexanedimethanol may further comprise a step of removing the solvent and by-products in the reaction product of step 2 to recover purified 1,4-cyclohexanedimethanol.

The step 3 is a purification step wherein solvents and by-products are removed in the reaction product of step 2, thus obtaining purified 1,4-cyclohexanedimethanol. Meanwhile, it is preferable that the second hydrogenation catalyst included in the reaction product of step 2 is removed by a filter, and the like, before conducting the step 3.

More specifically, the step 3 may comprises removing water in the 1,4-cyclohexanedimethanol composition comprising the reaction product of step 2, i.e., 1,4-cyclo-hexanedimethanol, water, and by-products; and removing by-products in the 1,4-cyclohexanedimethanol composition from which water has been removed.

By the purification step of the step 3, water and by-products may be removed to recover and obtain 1,4-cyclo-hexanedimethanol of high purity.

Thus, according to another embodiment of the invention, there is provided a composition comprising 1,4-cyclo-hexanedimethanol prepared by the method for preparing 1,4-cyclohexanedimethanol.

The composition of one embodiment may be used as the raw material of medicine, synthetic resin, synthetic fiber or dye.

Hereinafter, the invention will be explained in more detail through examples for better understanding of the invention. However, these examples are presented only as the illustrations of the invention, and the invention is not limited thereby.

EXAMPLE

Example 1

Step 1

A first reactor equipped with a gas-induced type stirrer was prepared.

In the reactor, 550 g of terephthalic acid(TPA), 92 g of hydrogenation catalyst Pd/C(comprising 5 wt % of Pd, based on the carrier carbon), and 2,100 g of solvent distilled water were introduced as reactants, and the inner atmosphere of the reactor was replaced with nitrogen, and then, the temperature of the mixed solution was raised to 250° C. while stirring at 50 rpm.

After the temperature of the mixed solution reached 250° C., in order to dissolve TPA, it was stirred for 30 minutes while maintaining the temperature. And then, the stirring speed was increased, and while supplying hydrogen in the reaction solution such that the internal pressure of the reactor is maintained at 120 bar, and surface area per unit volume of hydrogen gas is maintained at 300 to 500 m$^2$/m$^3$, a hydrogen reaction was conducted for 1 hour.

After the reaction was completed, a product comprising 569 g of 1,4-cyclohexanedimethanol(CHDA) (trans CHDA rate in CHDA: 68 wt %) and 2,100 g of water was obtained, and it was used as the reactant of the hydrogenation reaction of step 2, after removing only the hydrogenation catalyst by a metal filter.

Step 2

A second reactor equipped with a gas-induced type stirrer was prepared.

In the second reactor, 569 g of the reaction product of the step 1, i.e., CHDA (trans CHDA rate in CHDA: 68 wt %), 2,100 g of distilled water solvent, and 152 g of a catalyst (ruthenium-tin/carbon catalyst, comprising 5 parts by weight of ruthenium, and 5.8 parts by weight of tin, based on 100 parts by weight of a carbon carrier) were introduced, purged twice with nitrogen of 5 bar, and purged twice with hydrogen of 5 bar, and then, the temperature was raised to 230° C. while stirring at 50 rpm under hydrogen atmosphere (about 14-15 bar).

After reaching the reaction temperature, hydrogen was introduced to the reaction pressure of 100 bar, and then, the stirring speed was increased, and a reaction was conducted for 6 hours while maintaining the surface area per unit volume of hydrogen gas bubbles at 300 to 450 m$^2$/m$^3$.

Step 3

For the 1,4-cyclohexanedimethanol composition wherein the hydrogenation catalyst was removed in the reaction product of step 2 by a metal filter, water was evaporated in an evaporator under conditions of temperature of 50-60° C. and pressure of 10-20torr, thus first removing up to 95% of the initial water content, and for the 1,4-cyclohexanedime-thanol composition passing through the first water removal step, water was evaporated in a distillation apparatus under conditions of temperature of 100~420° C. and pressure of 0.01~0.001 torr, thus second removing up to 99% of the initial water content.

For the 1,4-cyclohexanedimethanol composition passing through the water removal step, by-products were removed in a distillation apparatus by distillation, thus obtaining purified 1,4-cyclohexanedimethanol.

Example 2

The same procedure as the step 1 of Example 1 was conducted, except that 286 g of terephthalic acid(TPA) was used in the step 1 of Example 1.

After completing the reaction of step 1, a product comprising 294 g of CHDA (trans CHDA rate in CHDA: 66 wt %) was obtained, and only the hydrogenation catalyst was removed with a metal filter, and then, it was used as the reactant of the hydrogenation reaction of step 2 to conduct the step 2 and step 3 of Example 1 were conducted.

Example 3

The same procedure as the step 1 of Example 1 was conducted, except that 378 g of terephthalic acid(TPA) was used in the step 1 of Example 1.

After completing the reaction of step 1, a product comprising 389 g of CHDA (trans CHDA rate in CHDA: 67 wt %) was obtained, and only the hydrogenation catalyst was removed with a metal filter, and then, it was used as the reactant of the hydrogenation reaction of step 2 to conduct the step 2 and step 3 of Example 1.

Example 4

The same procedure as the step 1 of Example 1 was conducted, except that 492 g of terephthalic acid(TPA) was used in the step 1 of Example 1.

After completing the reaction of step 1, a product comprising 506 g of CHDA (trans CHDA rate in CHDA: 69 wt %) was obtained, and only the hydrogenation catalyst was removed with a metal filter, and then, it was used as the reactant of the hydrogenation reaction of step 2 to conduct the step 2 and step 3 of Example 1.

Experimental Example

For the Examples, the yield, conversion, selectivity of CHDA, and the yield, conversion, selectivity of CHDM were calculated, and shown in the following Table 1.

1) Yield, conversion, selectivity of CHDA

Conversion=mole number of reacted TPA/mole number of supplied TPA

Selectivity=mole number of produced CHDA/mole number of reacted TPA

Yield=conversion×selectivity 15
16

2) Yield, conversion, selectivity of CHDM

Conversion=mole number of reacted CHDA/mole
number of supplied CHDA

Selectivity=mole number of produced CHDM/mole
number of reacted CHDA

Yield=conversion×selectivity

And, trans CHDA content in CHDA (the reaction product of step 1), and trans CHDM content in CHDM (the reaction product of step 2) were analyzed with gas chromatography (GC, column: HP-5, detector: FID).

TABLE 1

|  |  | Example 1 | Example 2 | Example 3 | Example 4 |
|---|---|---|---|---|---|
| Reaction of step 1 | Conversion of TPA(%) | 99.9 | 99.9 | 99.9 | 99.9 |
|  | Selectivity of CHDA(%) | 95 | 94.5 | 94.4 | 95 |
|  | Yield of CHDA(%) | 95 | 94.4 | 94.3 | 94.9 |
|  | Content of trans CHDA(wt %) | 68 | 66 | 67 | 69 |
| Reaction of step 2 | Conversion of CHDA(%) | 99 | 99 | 99 | 99 |
|  | Selectivity of CHDM(%) | 96 | 95 | 97 | 96 |
|  | Yield of CHDM(%) | 95 | 94 | 96 | 95 |
|  | Content of trans CHDM(wt %) | 74 | 69 | 71 | 74 |
| Reaction of step 3 | Purity of CHDM(wt %) | 99.8 | 99.7 | 99.7 | 99.8 |
|  | Content of trans CHDM(wt %) | 76 | 74 | 75 | 76 |

Referring to Table 1, it was confirmed that in the case of Examples 1 to 4 comprising a certain concentration of terephthalic acid, in CHDA obtained by the hydrogenation reaction of step 1, trans CHDA content was higher than 66 wt %, and thus, very high content of trans isomers were produced, and in CHDM obtained by the subsequent hydrogenation reaction of step 2, trans CHDM content was also very high (69 wt % or more).

What is claimed is:

1. A method for preparing 1,4-cyclohexanedimethanol (CHDM) comprising:
a step 1 wherein a reaction solution comprising terephthalic acid, a first hydrogenation catalyst, and water is supplied to a first reactor equipped with a stirrer, and a hydrogenation reaction is conducted to prepare 1,4-cyclohexane dicarboxylic acid (CHDA) comprising cis isomers and trans isomers; and
a step 2 wherein a reaction solution comprising a reaction product of the step 1, a second hydrogenation catalyst, and water is supplied to a second reactor equipped with a stirrer, and a hydrogenation reaction is conducted to prepare 1, 4-cyclohexanedimethanol (CHDM) comprising cis isomers and trans isomers, and
a step of removing the first hydrogenation catalyst included in the reaction product of the step 1, before conducting the step 2,
wherein the terephthalic acid is included in an amount of 12 to 22 wt %, based on a total amount of terephthalic acid and water, and
wherein the reaction product of step 1 comprises 1,4-cyclohexane dicarboxylic acid and water, and the 1,4-cyclohexane dicarboxylic acid is included in a content of 10 to 23 wt %, based on a total amount of 1,4-cyclohexane dicarboxylic acid and water, and
wherein a surface area per unit volume of hydrogen gas is maintained in a range of 15 m²/m³ to 500 m²/m³ during the hydrogenation reaction of the step 1 and the hydrogenation reaction of the step 2.

2. The method for preparing 1,4-cyclohexanedimethanol according to claim 1, wherein the hydrogenation reaction of the step 1 is conducted at a temperature of 230 to 300° C.

3. The method for preparing 1,4-cyclohexanedimethanol according to claim 1, wherein in the step 1, hydrogen gas is supplied at a pressure of 50 to 220 bar.

4. The method for preparing 1,4-cyclohexanedimethanol according to claim 1, wherein the first hydrogenation catalyst comprises one or more metals selected from the group consisting of palladium(Pd), rhodium(Rh), ruthenium(Ru), and platinum(Pt).

5. The method for preparing 1,4-cyclohexanedimethanol according to claim 1, wherein the 1,4-cyclohexane dicarboxylic acid comprises 60 wt % or more of trans isomers.

6. The method for preparing 1,4-cyclohexanedimethanol according to claim 1, wherein the hydrogenation reaction of the step 2 is conducted at a temperature of 230 to 300° C.

7. The method for preparing 1,4-cyclohexanedimethanol according to claim 1, wherein in the step 2, hydrogen gas is supplied at a pressure of 50 to 220 bar.

8. The method for preparing 1,4-cyclohexanedimethanol according to claim 1, wherein the second hydrogenation catalyst comprises one or more metals selected from the group consisting of palladium(Pd), rhodium(Rh), and ruthenium(Ru), and
one or more metals selected from the group consisting of tin(Sn), iron(Fe), rhenium(Re), and gallium(Ga).

9. The method for preparing 1,4-cyclohexanedimethanol according to claim 8, wherein the second hydrogenation catalyst comprises ruthenium(Ru) and tin(Sn).

10. The method for preparing 1,4-cyclohexanedimethanol according to claim 1, wherein the 1,4-cyclohexanedimethanol obtained in the step 2 comprises 63 wt % or more of trans isomers.

11. The method for preparing 1,4-cyclohexanedimethanol according to claim 1, further comprising a step 3 of removing water and by-products in a reaction product of the step 2 to recover purified 1,4-cyclohexanedimethanol.

12. The method of claim 1, wherein
in the step 1, the hydrogenation reaction of the step 1 is conducted at a temperature of 230 to 300° C. and hydrogen gas is supplied at a pressure of 50 to 220 bar,
the first hydrogenation catalyst comprises one or more metals selected from the group consisting of palladium (Pd), rhodium(Rh), ruthenium(Ru), and platinum(Pt),
in the step 2, the hydrogenation reaction of the step 2 is conducted at a temperature of 230 to 300° C. and hydrogen gas is supplied at a pressure of 50 to 220 bar,
the second hydrogenation catalyst comprises one or more metals selected from the group consisting of palladium (Pd), rhodium(Rh), and ruthenium(Ru), and one or more metals selected from the group consisting of tin(Sn), iron(Fe), rhenium(Re), and gallium(Ga), the reaction product of the step 1 and the reaction product of the step 2 each are generated without performing an isomerization reaction, a ratio of trans isomers in the CHDA of the reaction product of the step 1 is 60 wt % of more of trans isomers among the CHDA, a ratio of trans isomers in the CHDM of the reaction product of the step 2 is 63 wt % of more of trans isomers among the CHDM.

13. The method of claim 12, further comprising:

a step of removing the second hydrogenation catalyst from a reaction solution comprising the reaction product of the step 2.

14. The method of claim 13, wherein the surface area per unit volume of hydrogen gas is maintained in a range of 200 $m^2/m^3$ to 500 $m^2/m^3$ during the hydrogenation reaction of the step 1 and the hydrogenation reaction of the step 2.

15. The method of claim 12, wherein the ratio of trans isomers in the CHDA of the reaction product of the step 1 is higher than a ratio of trans isomers in the terephthalic acid in the reaction solution of the step 1, and the ratio of trans isomers in the CHDA of the reaction product of the step 1 is less than the ratio of trans isomers in the CHDM of the reaction product of the step 2.

\* \* \* \* \*